(12) United States Patent
Provost

(10) Patent No.: US 7,223,314 B2
(45) Date of Patent: May 29, 2007

(54) STRETCHABLE FASTENER

(75) Inventor: George A. Provost, Litchfield, NH (US)

(73) Assignee: Velcro Industries B.V., Caracao (NL)

( * ) Notice: Subject to any disclaimer, the term of this patent is extended or adjusted under 35 U.S.C. 154(b) by 751 days.

(21) Appl. No.: 10/242,900

(22) Filed: Sep. 13, 2002

(65) Prior Publication Data

US 2003/0034583 A1   Feb. 20, 2003

(51) Int. Cl.
B32B 38/04   (2006.01)
(52) U.S. Cl. .................. 156/259; 156/66; 156/244.11; 156/244.25; 156/244.18; 156/245; 156/264; 156/265; 156/271; 264/165; 264/167; 264/310
(58) Field of Classification Search ...................... None
See application file for complete search history.

(56) References Cited

U.S. PATENT DOCUMENTS

| | | |
|---|---|---|
| 3,000,384 A | 9/1961 | Piers, Jr. |
| 3,086,529 A | 4/1963 | Munz et al. |
| 3,113,803 A | 12/1963 | Struble et al. |
| 3,194,234 A | 7/1965 | Duckman et al. |
| 3,235,438 A | 2/1966 | Wisotzky |
| 3,341,386 A | 9/1967 | White et al. |
| 3,442,270 A | 5/1969 | Steinman |
| 3,594,863 A | 7/1971 | Erb |
| 3,594,865 A | 7/1971 | Erb |
| 3,608,035 A | 9/1971 | Frohlich |
| 3,665,921 A | 5/1972 | Stumpf |
| 3,665,922 A | 5/1972 | Skora |
| 3,705,065 A | 12/1972 | Stumpf |
| 3,708,361 A | 1/1973 | Stumpf |
| 3,880,161 A | 4/1975 | Fossel |
| 4,088,136 A | 5/1978 | Hasslinger et al. |
| 4,116,892 A | 9/1978 | Schwarz |
| 4,149,540 A | 4/1979 | Hasslinger |
| 4,154,889 A | 5/1979 | Platt |
| 4,181,127 A | 1/1980 | Linsky et al. |
| 4,207,885 A | 6/1980 | Hampton et al. |
| 4,223,059 A | 9/1980 | Schwarz |
| 4,247,967 A | 2/1981 | Swinton |
| 4,379,189 A | 4/1983 | Platt |
| 4,470,410 A | 9/1984 | Elliott |
| 4,522,853 A | 6/1985 | Szonn et al. |
| 4,569,348 A | 2/1986 | Hasslinger |
| 4,592,118 A | 6/1986 | DeWoskin |
| 4,654,246 A | 3/1987 | Provost et al. |
| 4,672,722 A | 6/1987 | Malamed |
| 4,761,318 A | 8/1988 | Ott et al. |

(Continued)

FOREIGN PATENT DOCUMENTS

DE   197 03 193 A1   1/1997

(Continued)

*Primary Examiner*—Jessica Ward
(74) *Attorney, Agent, or Firm*—Fish & Richardson P.C.

(57) ABSTRACT

Stretchable fastener products are formed by providing a sheet-form fastener tape, slitting the fastener tape to form longitudinally extending bands of fastener tape and separating the longitudinally extending bands to space the fastener tape bands transversely apart. The spaced bands are attached to a sheet form elastic web to form a stretchable fastener product. In some examples, the stretchable fastener product is formed continuously in conjunction with manufacture of the sheet-form fastener tape.

31 Claims, 13 Drawing Sheets

U.S. PATENT DOCUMENTS

| | | |
|---|---|---|
| 4,775,310 A | 10/1988 | Fischer |
| 4,794,028 A | 12/1988 | Fischer |
| 4,872,243 A | 10/1989 | Fischer |
| 4,894,060 A | 1/1990 | Nestegard |
| 4,920,235 A | 4/1990 | Yamaguchi |
| 4,931,344 A | 6/1990 | Ogawa et al. |
| 4,939,818 A | 7/1990 | Hahn |
| 4,972,829 A | 11/1990 | Knerr |
| 4,973,326 A | 11/1990 | Wood et al. |
| 4,984,339 A | 1/1991 | Provost et al. |
| 4,986,265 A | 1/1991 | Caponi |
| 5,015,251 A | 5/1991 | Cherubini |
| 5,048,158 A | 9/1991 | Koerner |
| 5,086,763 A | 2/1992 | Hathman |
| 5,106,362 A | 4/1992 | Gilman |
| 5,133,112 A | 7/1992 | Gomez-Acevedo |
| 5,137,508 A | 8/1992 | Engman |
| 5,142,743 A | 9/1992 | Hahn |
| 5,152,741 A | 10/1992 | Farnio |
| 5,167,613 A | 12/1992 | Karami et al. |
| 5,168,603 A | 12/1992 | Reed |
| 5,200,245 A | 4/1993 | Brodrick, Jr. |
| 5,234,462 A | 8/1993 | Pavletic |
| 5,260,015 A | 11/1993 | Kennedy et al. |
| 5,293,884 A | 3/1994 | Chapman et al. |
| 5,304,162 A | 4/1994 | Kuen |
| 5,318,555 A | 6/1994 | Siebers et al. |
| 5,321,855 A | 6/1994 | Ciuffo |
| 5,326,612 A | 7/1994 | Goulait |
| 5,383,872 A | 1/1995 | Roessler et al. |
| 5,386,595 A | 2/1995 | Kuen et al. |
| 5,403,302 A | 4/1995 | Roessler et al. |
| 5,403,413 A | 4/1995 | Masuda |
| 5,407,439 A | 4/1995 | Goulait |
| 5,415,626 A | 5/1995 | Goodman et al. |
| 5,423,789 A | 6/1995 | Kuen |
| 5,437,621 A | 8/1995 | Andrews et al. |
| 5,437,623 A | 8/1995 | McClees et al. |
| 5,441,687 A | 8/1995 | Murasaki et al. |
| 5,449,340 A | 9/1995 | Tollini |
| 5,456,660 A | 10/1995 | Reich et al. |
| 5,518,795 A | 5/1996 | Kennedy et al. |
| 5,531,732 A | 7/1996 | Wood |
| 5,535,787 A | 7/1996 | Howell |
| 5,542,942 A | 8/1996 | Kline et al. |
| 5,595,014 A | 1/1997 | Moore |
| 5,604,961 A | 2/1997 | Cole |
| 5,606,781 A | 3/1997 | Provost et al. |
| 5,615,460 A | 4/1997 | Weirich et al. |
| 5,624,427 A | 4/1997 | Bergman et al. |
| 5,624,429 A | 4/1997 | Long et al. |
| 5,643,651 A | 7/1997 | Murasaki |
| 5,656,111 A | 8/1997 | Dilnik et al. |
| 5,662,599 A | 9/1997 | Reich et al. |
| 5,669,120 A | 9/1997 | Wessels et al. |
| 5,669,901 A | 9/1997 | LaFortune et al. |
| 5,672,404 A | 9/1997 | Callahan, Jr. et al. |
| 5,700,340 A | 12/1997 | Johnson et al. |
| 5,722,968 A | 3/1998 | Datta et al. |
| 5,786,062 A | 7/1998 | Callahan, Jr. et al. |
| 5,807,300 A | 9/1998 | Nix, Jr. |
| 5,823,977 A | 10/1998 | Dalyea |
| 5,843,018 A | 12/1998 | Shesol et al. |
| 5,843,025 A | 12/1998 | Shaari |
| 5,843,057 A | 12/1998 | McCormack |
| 5,897,547 A | 4/1999 | Schmitz |
| 5,953,797 A | 9/1999 | Provost et al. |
| 5,961,761 A | 10/1999 | Heindel et al. |
| 6,035,498 A | 3/2000 | Buzzell et al. |
| 6,080,347 A | 6/2000 | Goulait |
| 6,115,891 A | 9/2000 | Suenaga et al. |
| 6,205,623 B1 | 3/2001 | Shepard et al. |

FOREIGN PATENT DOCUMENTS

| | | |
|---|---|---|
| EP | 0 605 013 A1 | 7/1994 |
| EP | 0 749 707 A1 | 12/1996 |
| EP | 0 780 505 A2 | 6/1997 |
| EP | 0 826 354 A2 | 3/1998 |
| FR | 2 750 319 | 1/1998 |
| GB | 2 296 423 | 7/1996 |
| JP | 8-187113 | 7/1996 |
| WO | WO 96/03101 A1 | 2/1996 |
| WO | WO 96/19960 | 7/1996 |
| WO | WO96/31180 | 10/1996 |
| WO | WO 97/25892 | 7/1997 |
| WO | WO 97/25893 | 7/1997 |
| WO | WO97/25953 | 7/1997 |
| WO | WO 99/17631 | 4/1999 |
| WO | WO 99/22619 | 5/1999 |
| WO | WO 99/48455 | 9/1999 |
| WO | WO 00/27235 | 5/2000 |
| WO | WO00/50229 | 8/2000 |
| WO | WO01/67911 | 9/2001 |

MACHINE DIRECTION 60
SEPARATOR

SEPARATOR

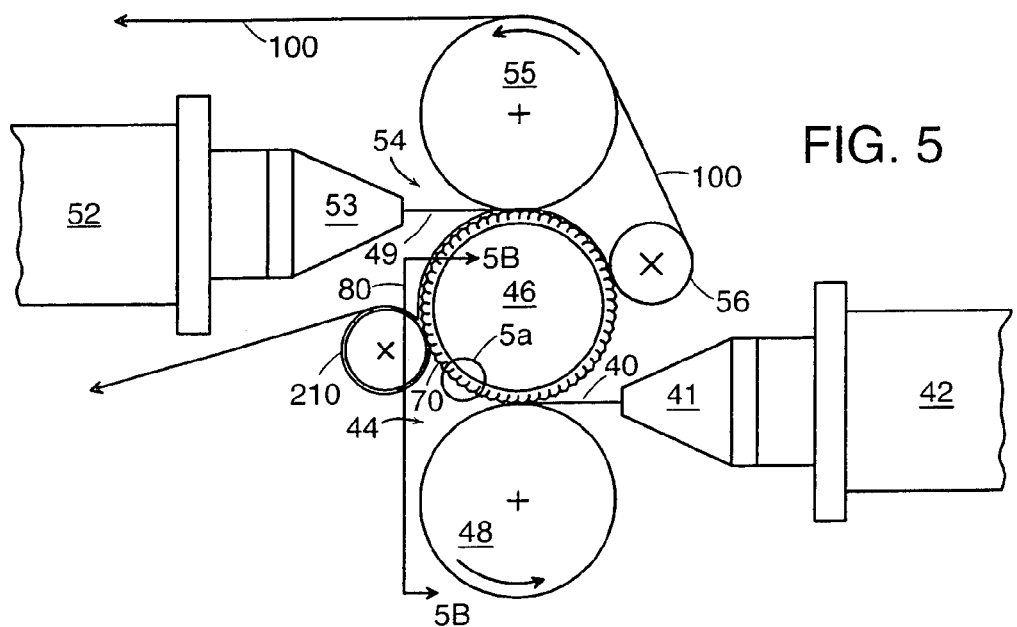
FIG. 5
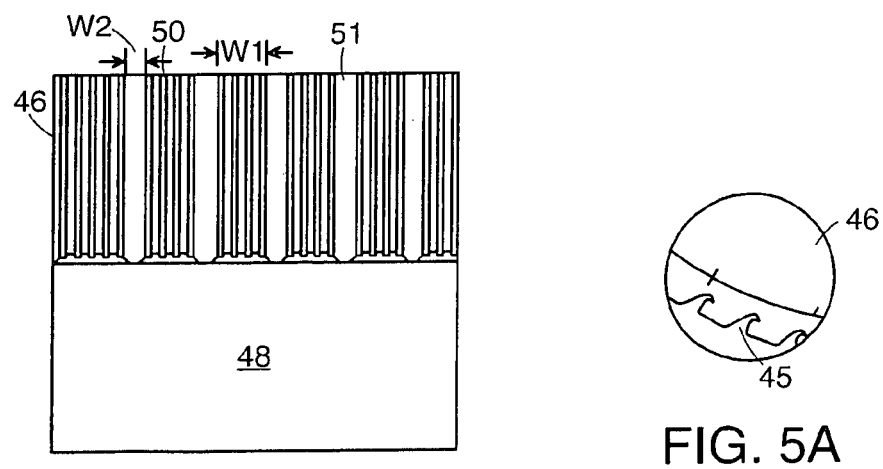
FIG. 5B
FIG. 5A

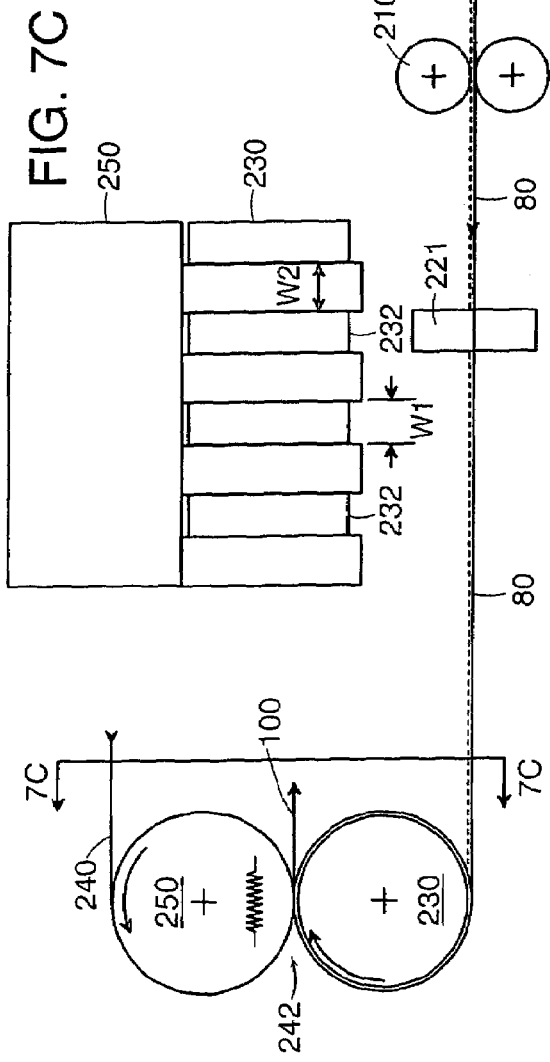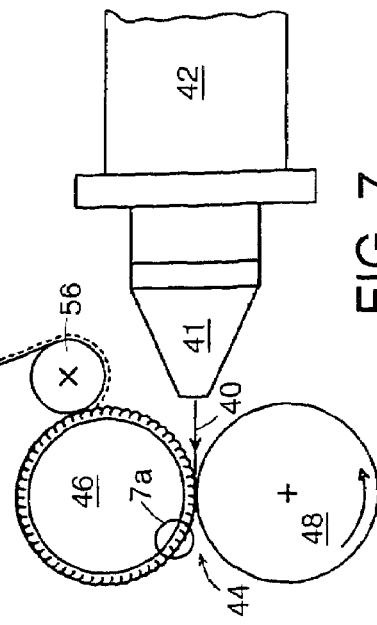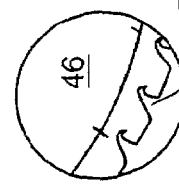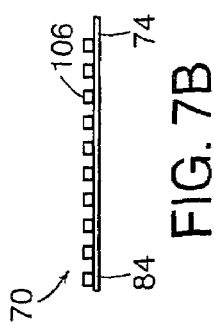

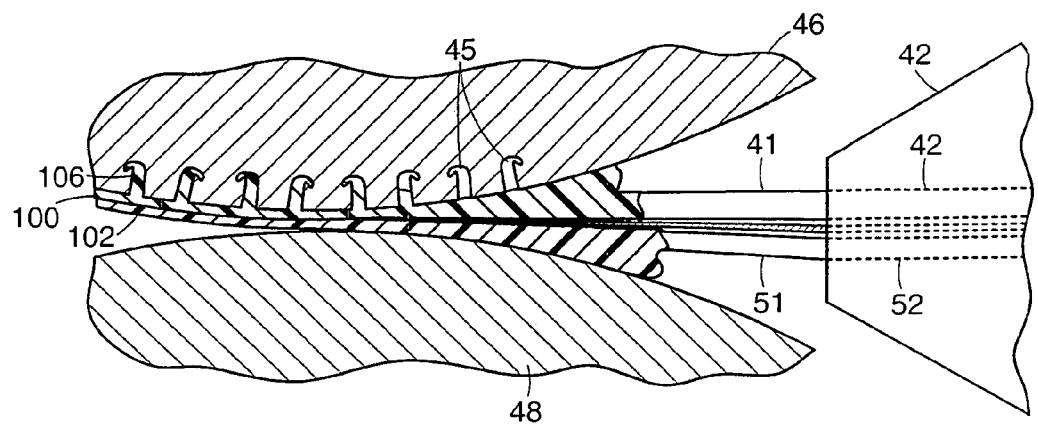
FIG. 10B
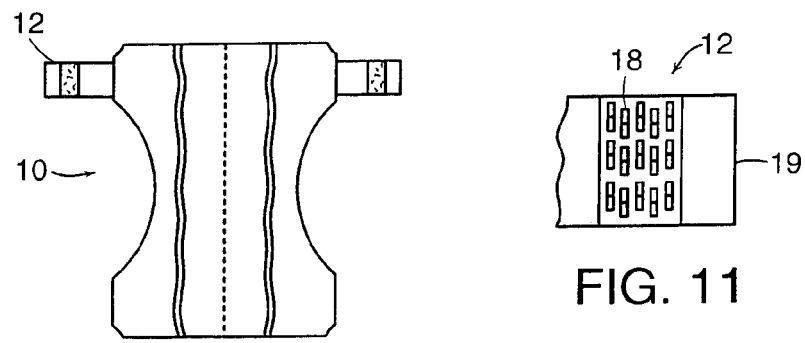
FIG. 11A
FIG. 11

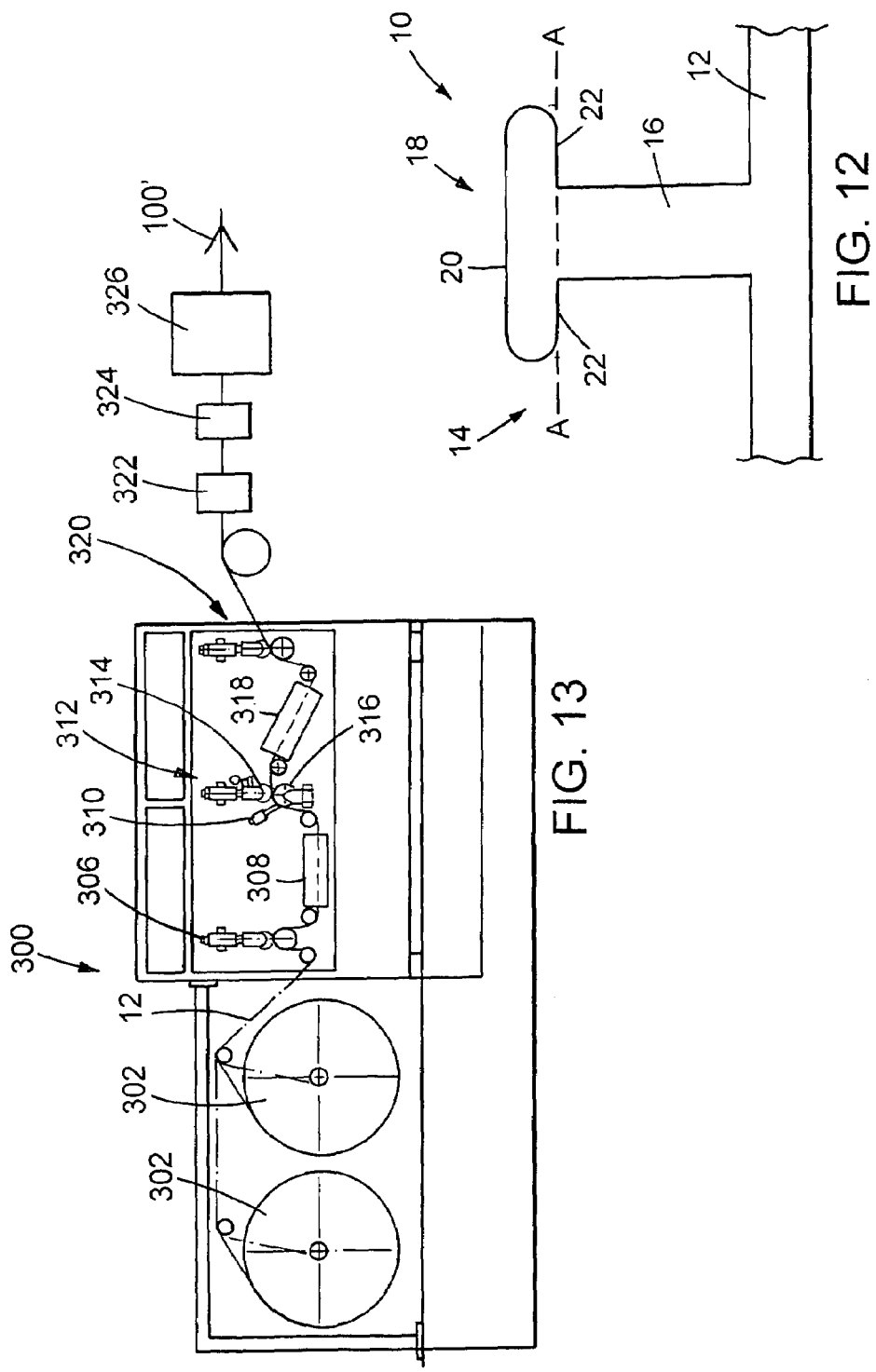

STRETCHABLE FASTENER

CLAIM OF PRIORITY

This application claims priority under 35 USC § 120 to PCT/US01/07939, filed Mar. 12, 2001, which claims priority from U.S. Patent Application Ser. No. 60/189,136, filed on Mar. 14, 2000, the entire contents of both of which are hereby incorporated by reference.

TECHNICAL FIELD

This invention relates to stretchable fasteners and especially to stretchable fasteners that may be practical and cost efficient for fastening applications where elasticity and flexibility is desired.

BACKGROUND

Stretchable fasteners that carry hook and loop closures are desirable as part of infant and adult diapers, surgical gowns, and other garments and wraps. The fasteners typically comprise sheet, film or non-woven webs of elastic construction that have embossing or other surface patterns for grasping by the user. To the back of such an elastic web, a tape of fastener elements is secured, forming a laminate structure. The fastener tape is typically made of a synthetic resin that is not stretchable, and the resulting laminate is relatively stiff, does not stretch, and does not present the desired degree of cloth-like feel.

It is desirable that the substance of the tab and the associated fastener tape provide an integral, stretchy component that achieves the desired qualities, such as elasticity, flexibility and cloth-like feel.

SUMMARY

The invention features, in several of its aspects, a method of forming stretchable fasteners. The fasteners have a base of synthetic resin, and an array of loop-engageable fastener elements integrally molded with and extending from the base.

According to one aspect of the invention, a method of forming a stretchable fastener product includes providing a sheet-form fastener tape, processing the fastener tape including slitting to form longitudinally extending bands of fastener tape and to space said fastener bands transversely apart, and attaching the transversely spaced apart fastener bands to a sheet form elastic web.

In some cases, the elastic web extends across the fastener bands as well as across spaces between adjacent spaced apart bands and in other cases the elastic web extends only across spaces between adjacent spaced apart bands.

Transversely spaced apart bands are formed by passing the slit fastener tape bands through a separator that separates the bands and spaces them transversely apart, or by removing every other adjacent band of the slit fastener tape bands. The transversely spaced apart fastener bands are attached to the elastic web by thermal fusion, ultrasonic welding, or an adhesive. In one embodiment, the every other adjacent band that has been removed is attached to a second sheet form elastic web to form a second stretchable fastener.

Certain, exemplary embodiments of the invention have one or more of the following features. The fastener tape comprises a base of synthetic resin, and an array of loop-engageable fastener elements integrally molded with and extending from a first surface of the base. The array of loop-engageable fastener elements has a density of the order of 500 or more fastener elements per square inch. The array of loop-engageable fastener elements has a density of the order of 1000 or more fastener elements per square inch. The fastener elements have relatively stiff stems and hook-shaped heads and in some instances the stems have a greater cross-section than the hook-shaped heads. The fastener elements have relatively stiff stems and disc-shaped heads. The disc-shaped heads have a flat top surface.

In some embodiments, the transversely spaced apart fastener bands are attached to the elastic web by supporting the spaced apart fastener bands on a support roll, wherein the loop-engageable fastener elements are in contact with a surface of the support roll, while simultaneously pressing and heating the elastic web against a second surface of the base of the fastener tape bands. A heated laminating roll or a continuous belt is arranged to press the elastic web against the second surface of the base of the fastener bands to promote lamination.

The support roll may have circumferential recesses, which are configured to support the fastener bands and to position the second surface of the base of the fastener bands at the surface of the support roll.

In some cases, a backing is attached to the second surface of the base of the fastener bands. The backing may be a heat-sensitive adhesive, and the method then includes the step of activating the adhesive before engagement with the elastic web.

According to another aspect of the invention, a stretchable fastener product is formed by first introducing a moldable first material to a continuously rotating mold roll to form a sheet-form fastener having a base conforming to a surface of the mold roll and multiple rows of molded fastener elements integral with the base. The rows extend in a longitudinal direction of the sheet-form fastener and the fastener elements are formed by mold cavities of the mold roll. The thus-formed sheet-form fastener is then slit into longitudinally extending band portions carrying multiple rows of the fastener elements. Spaces are then created between adjacent bands transverse to the longitudinal direction, and subsequently a web of a second material different from the material of the fastener elements is joined to the transversely spaced apart bands.

Exemplary embodiments may have one or more of the following features. The second material is resiliently extensible. The slit bands of the fastener product are removed from the mold roll, and are passed through a separating device that develops space between the adjacent bands transversely to the longitudinal direction. Thereafter the bands are introduced onto a surface of a support roll, and the web of the second material is joined to the bands by pressure and heat while the fastener bands are on the support roll. The support roll may have circumferential recesses, which are configured to support the fastener bands and to position the second surface of the base of the fastener bands at the surface of the support roll.

In some embodiments the fastener elements are loop-engageable hooks molded of synthetic resin of density of the order of 1000 or more fastener elements per square inch. The fastener elements may have relatively stiff stems of greater cross-section than their loop-engageable hooks. The hooks of the fastener elements of a given band may engage the bottom of the respective recess and may be collectively self supporting under the pressure of laminating, serving to assist in producing laminating pressure by which the bands are joined to the second material. A heated laminating roll or a continuous belt is arranged to press the second material against the second surface of the fastener bands to promote lamination.

In some embodiments a sheet-form fastener is formed on the mold roll having bands of fastener elements spaced apart from bands of material to be removed. The sheet-form fastener is then slit and the bands of material to be removed are removed while the bands of fastener elements remain on the mold roll. While the fastener elements thus continue to reside in their respective mold cavities, and with the mold roll serving as a pressure roll, a second material is joined to the bands. The second material is a molten resin introduced to the mold roll into contact with regions vacated by the bands of material that have been removed. Portions of the mold roll corresponding to the spaces between the bands of fastener elements may be substantially smooth cylindrical sections. In some cases the second material is introduced across the width of the bands of fastener elements as well as the vacated spaces between the bands of fastener elements.

In some embodiments, a second parallel roll forms a nip with the mold roll, and an extruder is arranged to deliver molten resin to the nip to serve as the second material, the nip being effective to apply the resin as a layer that bridges between the bands of fastener material.

The fastener elements are loop engageable hooks molded of resin selected from the group consisting of polyester, polyethylene, polypropylene, polyamide and copolymers and alloys thereof. The second material is comprised of a resilient resin having an elongation in the range of 50% to 300% and a recovery of at least 75%. The second material is selected from the group consisting of thermoplastic elastomers, thermoplastic polyurethanes, elastomeric copolymers containing polyethylene terephthalate (PET), thermoplastic olefins, and natural or synthetic rubber. The second material may also be a preformed nonwoven loop material, the loop material being releasably engageable by the fastener tape. The nonwoven material may be a needled web having a basis weight of less than about 4 oz/square yard.

In some embodiments, each of the fastener bands and spaces between the fastener bands has a width of ¼ inch (6.4 mm) or less. In other embodiments each of the fastener bands and spaces between the fastener bands has a width greater than ¼ inch (6.4 mm). In other embodiments, each of the fastener bands has a width less than or equal to ¼ inch (6/4 mm), and each of the spaces between the fastener bands has a width greater than or equal to ¼ inch (6.4 mm). In yet other embodiments, each of the fastener bands has a width greater than or equal to ¼ inch (6/4 mm), and each of the spaces between the fastener bands has a width less than or equal to ¼ inch (6.4 mm).

According to another aspect of the invention, a method of forming a stretchable fastener product is disclosed, the method including introducing a moldable first material to a continuously rotating mold roll to form a sheet-form product having a base conforming to a surface of the mold roll and multiple rows of stem elements integral with the base, the rows extending in a longitudinal direction of the sheet-form fastener, the stems formed by mold cavities of the mold roll. The method also includes heating a tip portion of the stems, contacting a cooled roller to the tip portion of the stems to produce disc-shaped engaging heads on the stems, slitting the thus-formed sheet-form fastener into longitudinally extending band portions carrying multiple rows of the fastener elements, creating space between adjacent bands transverse to the longitudinal direction, and subsequently joining to the transversely spaced apart bands a web of a second material different from the material of the fastener elements.

An exemplary embodiment of this aspect of the invention may include creating space between adjacent bands by directing selected bands to a first station and directing bands adjacent the selected bands to a second station, whereby the selected bands form a first set of transversely spaced apart bands and the bands adjacent the selected bands form a second set of transversely spaced apart bands, each of the first and second stations being provided for performing the joining operation, whereby the first set is laminated to a first web of the second material to form a first stretchable fastener product and the second set is joined to a second web of the second material to form a second stretchable fastener product. Other variations of this aspect of the invention can include any of the features described above with reference to other aspects of the invention.

Another aspect of the invention is a method of simultaneously forming multiple stretchable fastener products including providing a sheet-form fastener tape, slitting the sheet-form fastener tape to form longitudinally extending bands of fastener tape, directing a first set of the bands to a first attachment station and directing a second set of the bands to a second attachment station, the bands of the first and second sets being selected so that each set comprises transversely spaced apart fastener bands, and attaching the first set of transversely spaced apart fastener bands to a sheet form elastic web at the first attachment station and attaching the second set of transversely spaced apart fastener bands to a sheet form elastic web at the second station to simultaneously form multiple stretchable fastener products.

Variations of this aspect of the invention can include any of the features described above with reference to other aspects of the invention.

According to another aspect of the invention, a stretchable fastener product is provided by employing one of the above-described methods. The stretchable fastener has an elastic web, and multiple fastener tape bands attached to the elastic web and configured to be oriented parallel to each other and spaced apart from each other.

Variations of this aspect of the invention can include any of the features described above with reference to other aspects of the invention.

In some embodiments, each fastener band comprises a base of synthetic resin, and an array of loop-engageable fastener elements integrally molded with and extending from a first surface of the base. The array of loop-engageable fastener elements may have a density of the order of 1000 or more fastener elements per square inch. The fastener elements may have relatively stiff stems and hook-shaped heads, and the stems may have greater cross-section than the hook-shaped heads. A backing may be attached to a second surface of the base, and the backing may be a heat-sensitive adhesive. The resin may be selected from the group consisting of polyester, polyethylene, polypropylene, polyamide and copolymers and alloys thereof. The elastic web may be made of a resilient resin and may have an elongation in the range of 50% to 300% and a recovery of at least 75%. The elastic web may be selected from the group consisting of thermoplastic elastomers, thermoplastic polyurethanes, elastomeric copolymers containing PET, thermoplastic olefins, and natural or synthetic rubber.

The elastic web may be a preformed nonwoven loop material, and the nonwoven material may be a needled web having a basis weight of less than about 4 oz/square yard.

The fastener bands and spaces between the fastener bands may each be of the order of ¼ inch or less wide and ¼ inch or less wide, respectively.

According to another aspect of the invention, a stretchable fastener product includes multiple fastener tape bands and multiple elastic web bands, and edge margins of the elastic web bands are attached to edge margins of the fastener bands. The edge margins of the elastic web bands may overlap or abut the edge margins of the fastener bands.

Among the advantages of the invention may be one or more of the following. The stretchable fasteners of this invention do not "set", i.e., stretch partially irreversibly, have hooks with strong structural integrity and are cost efficient.

Other features and advantages of the invention will be apparent from the following description of embodiments, and from the claims.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 5 illustrates another method and another apparatus for forming the stretchable fastener of FIG. 1.

FIG. 5A is an expanded view of area 5A in FIG. 5.

FIG. 5B is a cross sectional view of the apparatus in FIG. 5 taken in plane 5B-5B.

FIG. 7 illustrates another method and an apparatus for forming the stretchable fastener of FIG. 1.

FIG. 7A is an expanded view of area 7A in FIG. 7.

FIG. 7B is a side view of the fastener tape 70 in FIG. 7.

FIG. 7C is a cross sectional view of the apparatus in FIG. 7 taken in plane 7C-7C.

FIG. 10B is an expanded view of the nip area 44 in FIG. 10.

FIG. 11 is a top view of a stretchy diaper tab.

FIG. 11A illustrates a diaper with a stretchy diaper tab.

FIG. 12 is a side view of an alternative fastener element that can be used for the stretchable fastener of FIG. 1.

FIG. 13 is a diagrammatic illustration of a method and apparatus for making a stretchable fastener similar to that of FIG. 1, but having fastener elements similar to that of FIG. 12.

Like reference symbols in the various drawings indicate like elements.

DETAILED DESCRIPTION

Figure 1:
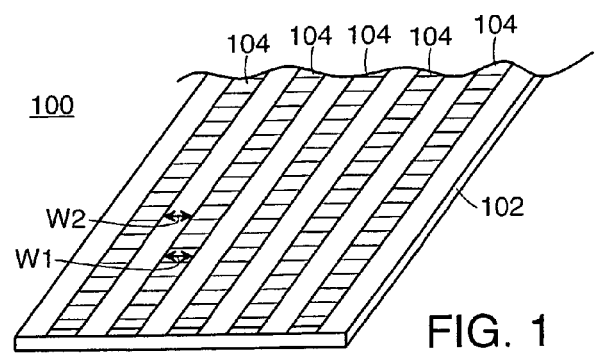
FIG. 1 is a perspective view of a stretchable fastener having spaced apart bands of fastener tape attached onto an elastic substrate.
Figure 1A:
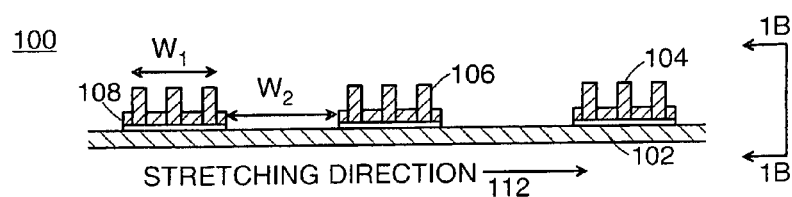
FIG. 1A is an expanded side view of the stretchable fastener of FIG. 1.
Figure 1B:
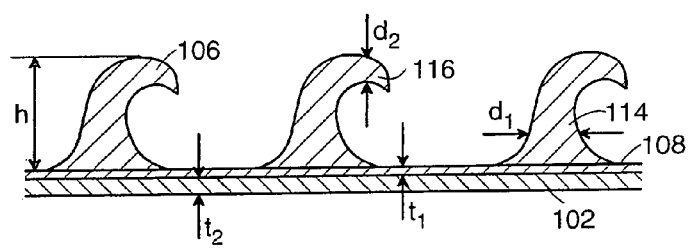
FIG. 1B is an expanded side view of the stretchable fastener of FIG. 1A taken in plane 1B-1B.
Figure 1C:
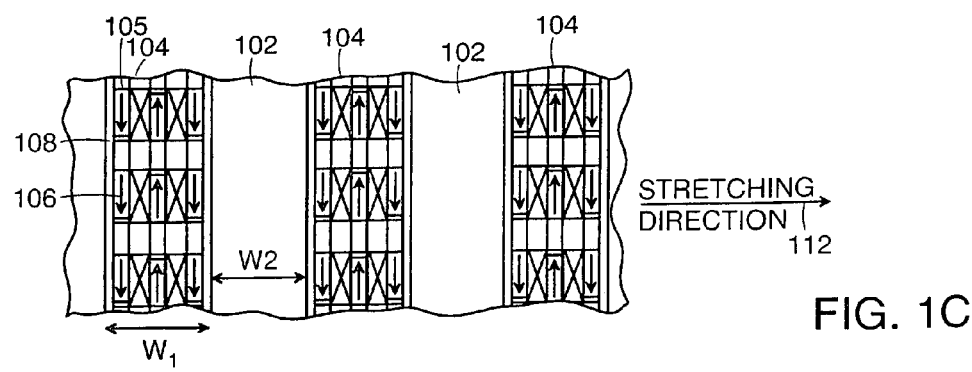
FIG. 1C is an expanded top view of the fastener of FIG. 1.

Referring to FIGS. 1 and 1A, a stretchable fastener 100 features spaced apart bands of fastener tape 104, attached to a sheet-form elastic substrate 102. Each fastener band 104 has a width w1 of the order of ⅛ inch and is spaced apart from a neighboring fastener band by a distance w2 of the order of ⅛ inch. Each fastener band has rows 105 of fastener elements 106 integral with a base layer 108 (FIG. 1A). During use of the stretchable fastener a stress is applied along a stretching direction 112. The applied stress causes an elongation of the elastic layer 102 parallel to the stretching direction, and when the stress is removed the fastener 100 returns to its original dimensions. In this embodiment, the fastener elements are in the form of J-hooks and extend in rows 105 perpendicular to the stretching direction 112. The J-hooks have a stiff stem 114 and a hook shaped head 116 (FIG. 1B) pointing in the direction of the arrows (FIG. 1C) and perpendicular to the stretching direction 112. Adjacent rows of hooks 105 have oppositely oriented hooks 106, as shown in FIG. 1C. The cross-sectional diameter of the stem d1 is greater than the cross-sectional diameter of the hook shaped head d2.

In one example, the hooks are of CFM-29 designation, available from Velcro USA Inc. of Manchester, N.H., U.S.A. The CFM-29 hook strip has hooks of only 0.015 inch (0.38 mm) height h, a base thickness t1 of 0.003 inch (0.08 mm) and a fastener element density of the order of 1000 or more fastener elements per square inch. The thickness t2 of the elastic substrate is 0.005 inch (0.13 mm) (FIG. 1B).

The elastic layer 102 is composed of a thermoplastic elastomer, such as Santoprene☐, having an elongation in the range of 50% to 300% and a recovery of at least 75%. The fastener bands 104 are composed of a synthetic resin such as, polypropylene, polyethylene terephthalate (PET), polyethylene, nylon and polyvinyl chloride (PVC), among others. The fastener bands are attached to the elastic layer by thermal fusion generated by ultrasonic or thermal welding.

Figure 1D:
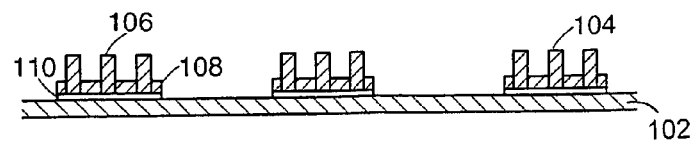
FIG. 1D is an expanded side view of another embodiment of a stretchable fastener.

In the embodiment of FIG. 1D, the fastener bands 104 have a backing layer 110 attached to a surface of the base layer 108 opposite the surface with the fastener elements 106. The backing layer 110 is composed of a resin that facilitates the fusion between the base layer 108 and the elastic layer 102. In some instances, the backing layer 110 is an adhesive that bonds the base layer 108 to the elastic layer 102.

Figure 2:
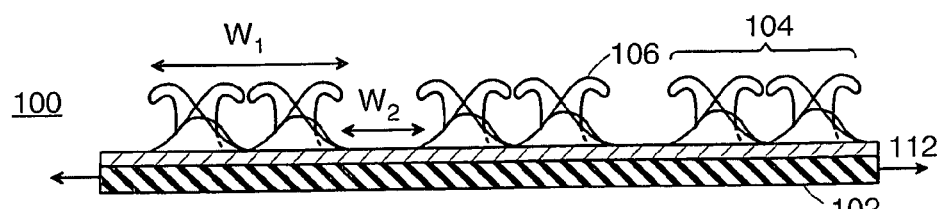
FIG. 2 is an expanded side view of another embodiment of a stretchable fastener having spaced apart bands of fastener tape attached onto an elastic substrate.
Figure 2A:
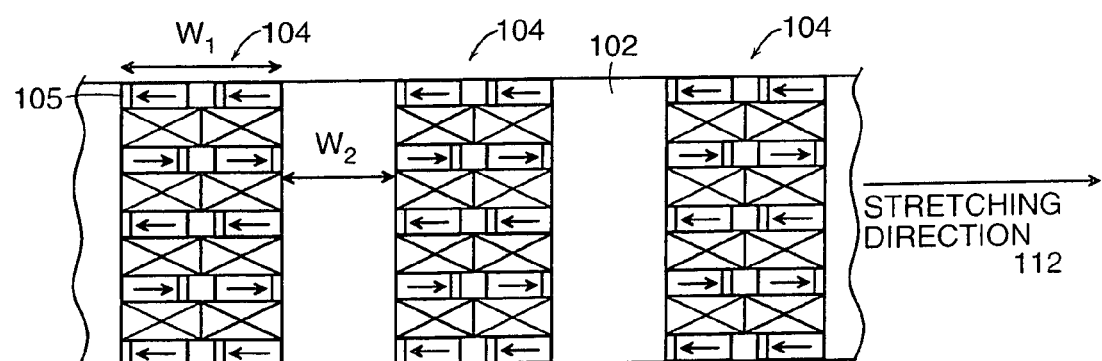
FIG. 2A is an expanded top view of the fastener of FIG. 2.

Referring to FIGS. 2 and 2A, a stretchable fastener 100 features spaced apart bands of fastener tape 104, attached to a sheet-form elastic substrate 102. Each fastener band has rows 105 of fastener elements 106 integral with a base layer 108 (FIG. 2A). The fastener elements 106 are in the form of J-hooks and extend in rows 105 perpendicular to the stretching direction 112. The J-hooks have a stem 114 and a hook shaped head 116 (FIG. 1B) pointing in the direction of the arrows (FIG. 1C) and parallel to the stretching direction 112.

Figure 9:
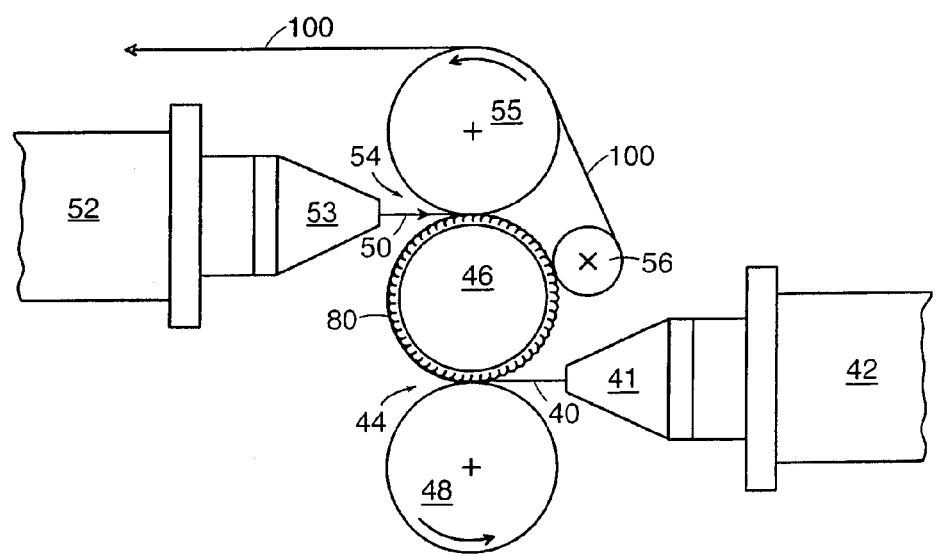
FIG. 9 illustrates another method and an apparatus for forming the stretchable fastener of FIG. 9B.
Figure 9A:
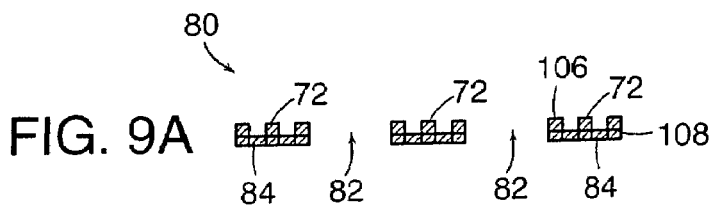
FIG. 9A is a side view of the molded fastener bands 80 in FIG. 9.
Figure 9B:
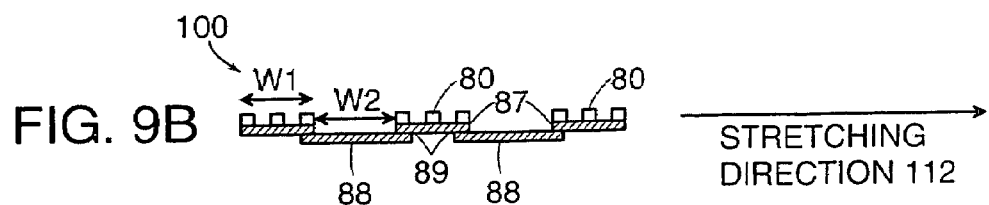
FIG. 9B is a side view of a stretchable fastener having spaced apart fastener bands attached to elastic bands.
Figure 9C:
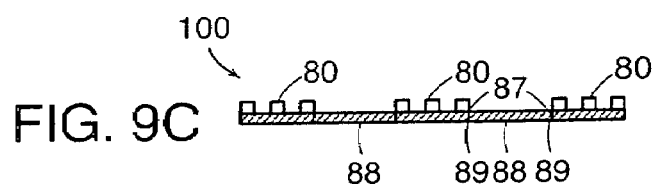
FIG. 9C is a side view of another embodiment of a stretchable fastener having spaced apart fastener bands attached to elastic bands.

Referring to FIGS. 9B and 9C, a stretchable fastener 100 features spaced apart fastener tape bands 80, joined together by bands of an elastic substrate 88. The elastic substrate bands 88 have edge margins 89 overlapping (FIG. 9B) or abutting (FIG. 9C) edge margins 87 of the fastener bands 80. Each fastener band 80 has rows 72 of fastener elements 106 integral with a base layer 108 (FIG. 2A). The fastener elements 106 are in the form of J-hooks and extend in rows 72 perpendicular to the stretching direction 112.

Figure 3:
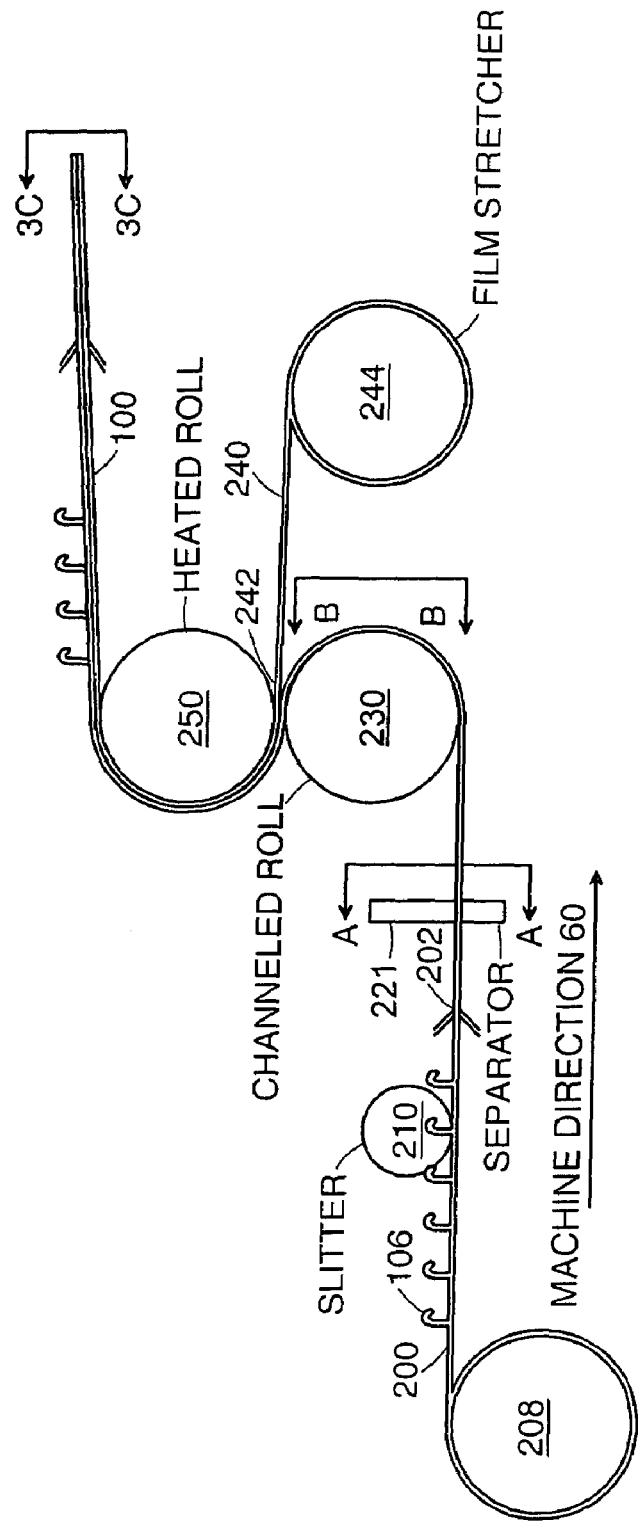
FIG. 3 illustrates a method and an apparatus for forming the stretchable fastener of FIG. 1.
Figure 3A:
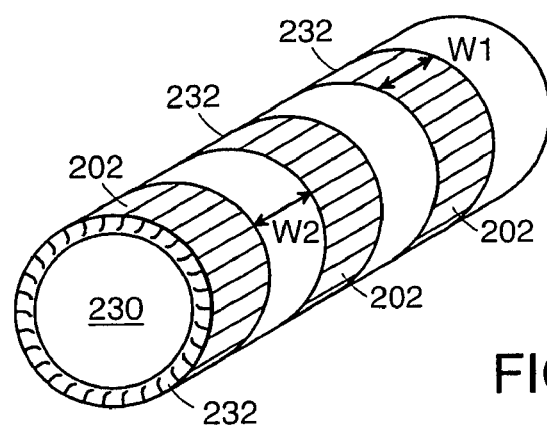
FIG. 3A is an expanded perspective view of the channeled roll 230 in FIG. 3.
Figure 3B:
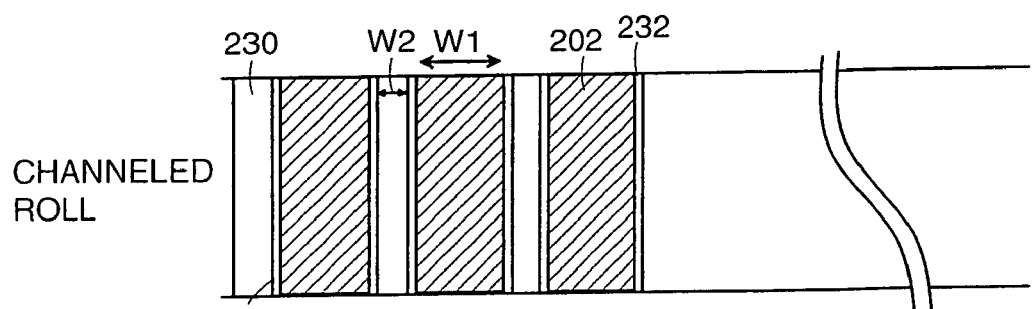
FIG. 3B is a side view of a channeled roll taken in plane 3B-3B of FIG. 3.
Figure 3C:
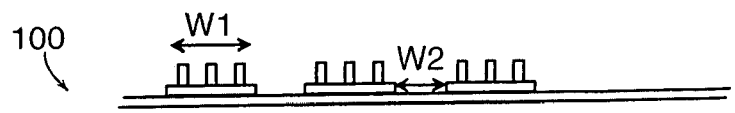
FIG. 3C is a cross sectional view of a stretchable fastener taken in plane 3C-3C of FIG. 3.

The products of FIGS. 1 and 2 may be economically formed by the process and apparatus illustrated in FIG. 3. A sheet-form fastener 200, supplied by roll 208, is slit by slitter 210 to form fastener tape bands 202 extending in a longitudinal direction. The slit fastener bands 202 subsequently pass through a separator 221. Separator 221, separates the slit fastener bands 202 and spaces them apart transverse to a machine direction 60. The spaced apart fastener bands are then introduced into spaced apart channels 232 formed on the surface of the channeled roll 230 (FIGS. 3A and 3B). The hook-shaped fastener elements 106 have relatively stiff stems with greater cross-section than the loop-engageable hooks and reside in the channels 232. The hooks of the fastener elements of a given band engage the bottom of the respective channel 232. The channels 232 have a width equal to the fastener band width w1 and are spaced apart by a distance equal to the fastener band spacing w2. The fastener bands travel around a segment of the periphery of the channeled roll 230 and are introduced into a nip 242, formed between the channeled roll 230 and a heated pressure roll 250. Simultaneously with the fastener bands, a sheet-form elastic web 240 is introduced into the nip 242. The heated roll presses and fuses the elastic web 240 onto the back surface of the fastener bands 202. The hooks engaging the bottom of the channels 232 are collectively self-supporting under the pressure of laminating and assist in producing the laminating pressure by which the bands are joined to the second material. The composite elastic web with the attached fastener bands 100 is then removed from the heated roll 250.

Figure 3D:
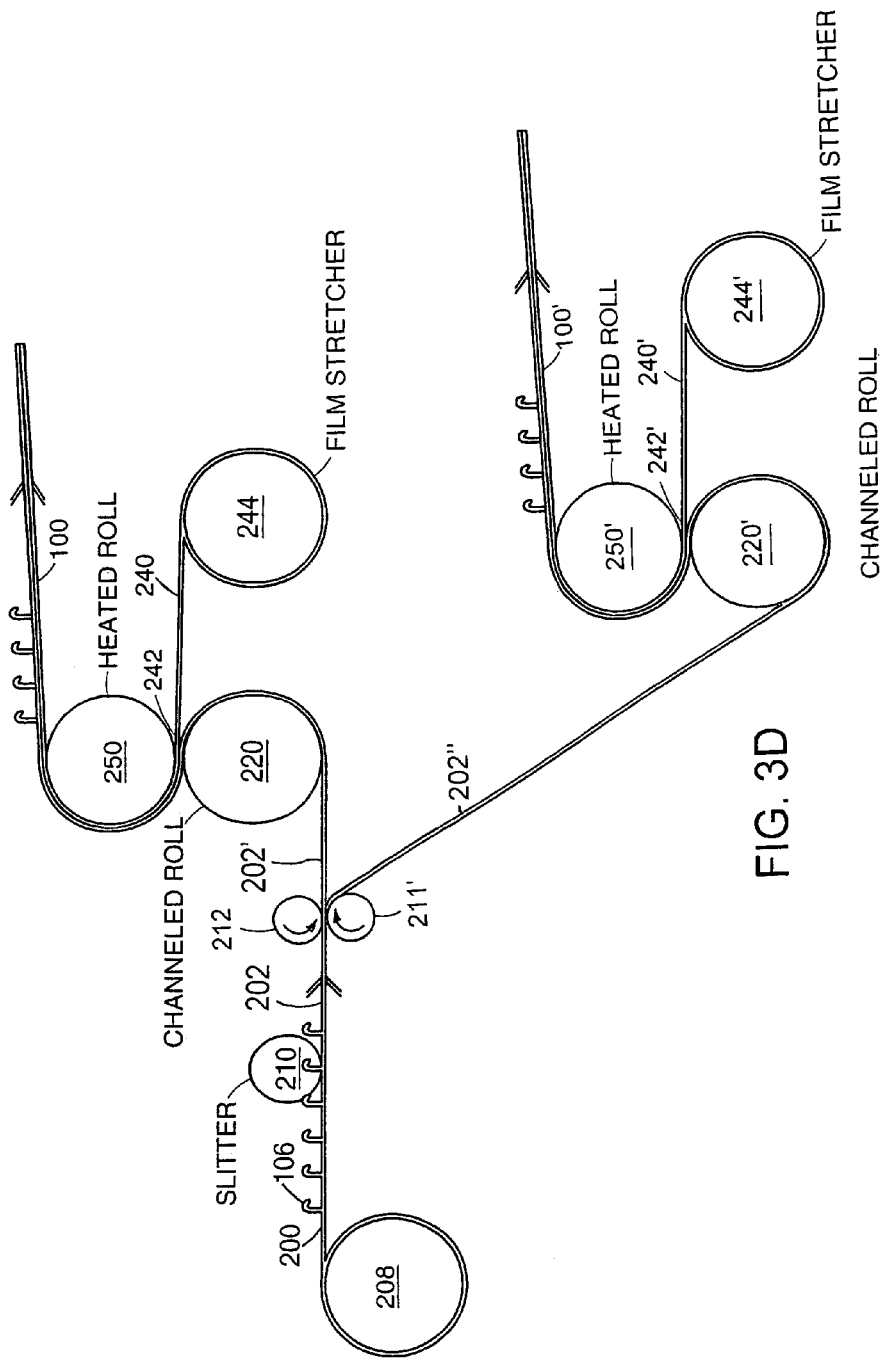
FIG. 3D illustrates a variation of the method and apparatus of FIG. 3.

As illustrated in FIG. 3D, the method and apparatus described above with reference to FIG. 3 can be modified to remove separator 221. Sheet-form fastener 200, after being slit by slitter 210 to form fastener tape bands 202 passes through tensioning nip rolls 211 and 212 where selected tape bands 202' are directed to channeled roll 220 while tape bands 202" adjacent to selected tape bands 202' are directed to another channeled roll 220'. The processing of each set of tape bands 202', 202" then proceeds in a similar manner to that described above, except the two sets of tape bands 202', 202" are processed in parallel. Accordingly, elastic film is provided by two respective film stretchers 244, 244' and lamination is carried out by two respective heated rolls 250, 250' that form respective nips 242, 242' with channeled rolls 220, 220'. The parallel processing yields two completed elastic fastener products 100, 100'.

While the example illustrated in FIG. 3D illustrates simultaneous production of two elastic fastener products, similar arrangements with three or more sets of apparatus for parallel processing of a corresponding sets of spaced bands can also be achieved.

Figure 4:
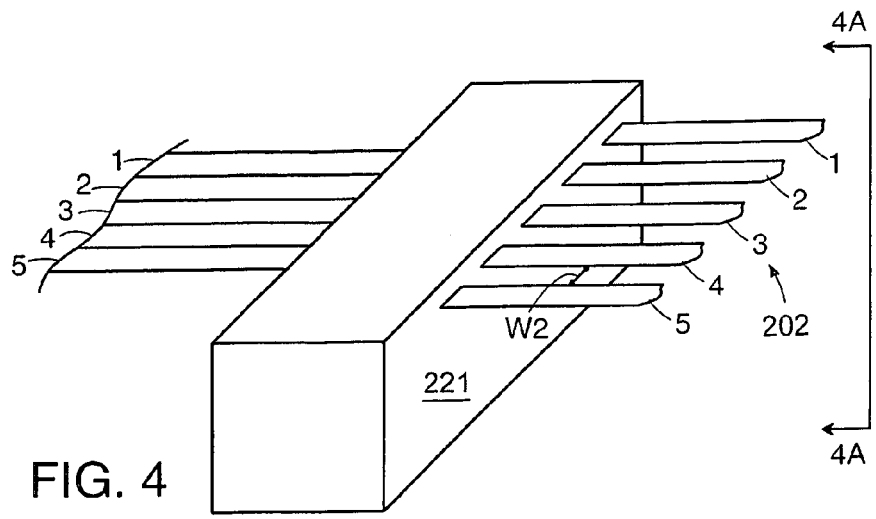
FIG. 4 is a perspective view of a separator that spreads apart the incoming slit fastener bands.
Figure 4B:
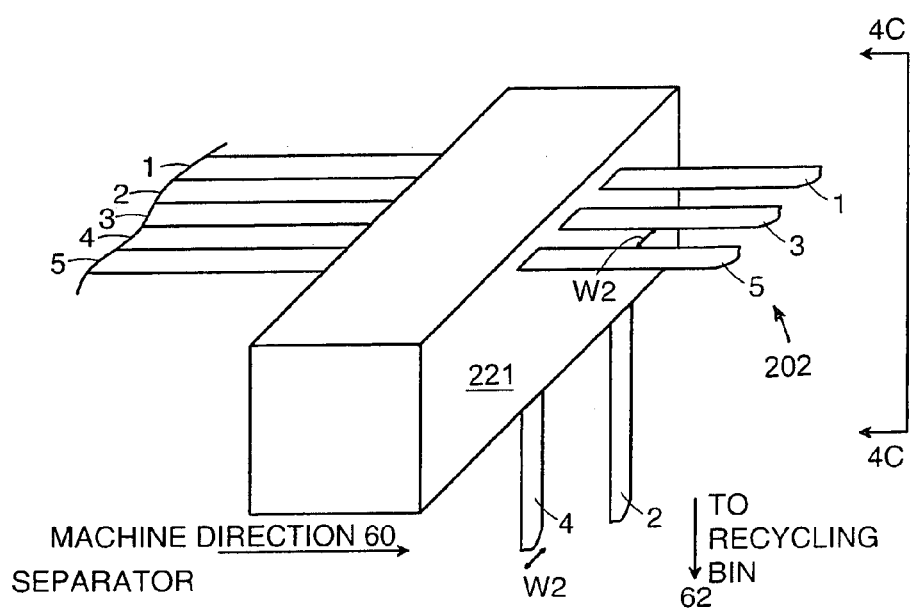
FIG. 4B is a perspective view of a separator that creates spaces between the adjacent slit fastener bands by removing every other band of the incoming slit bands.
Figure 4A:
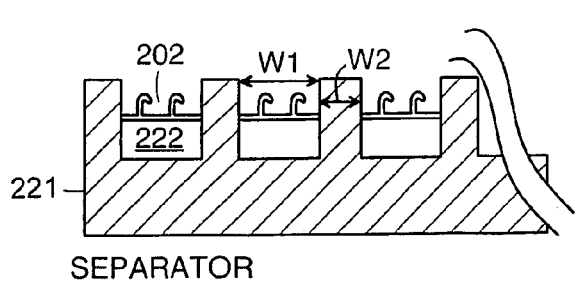
FIGS. 4A is a cross sectional view of a separator taken in plane 4A-4A of FIG. 4.

Referring to FIGS. 4 and 4A, the separator 221 has spaced apart openings 222 and is configured to receive the adjacent slit fastener bands 1 to 5 and place each one in a separate opening. There are at least as many openings as the number of slit fastener bands and each opening has a width at least equal to the fastener band width w1. The spacing w2 between openings 222 corresponds to the desired spacing of the fastener bands 202 in the stretchable fastener 100. By passing though the spaced apart openings, fastener bands 1 to 5 are separated and exit the separator 221 spaced apart at a distance w2.

Figure 4C:
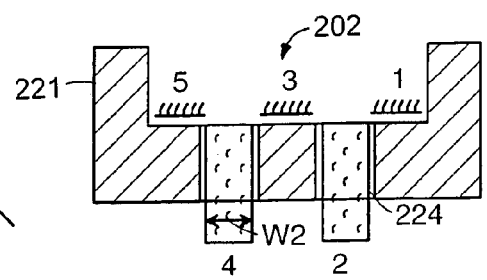
FIG. 4C is a cross sectional view of the separator in FIG. 4B taken in plane 4C-4C in FIG. 4.

In the embodiment shown in FIGS. 4B and 4C, the separator 221 is configured to separate incoming slit bands 1 to 5 by removing every other band, i.e., bands 2 and 4 are removed and bands 1, 3 and 5 exit the separator spaced apart by a distance w2 corresponding to the width of the removed bands. Bands 2 and 4 are introduced into openings 224, formed in the separator 221. Openings 224 are oriented perpendicular to the machine direction and direct bands 2 and 4 toward the recycling bin. Alternatively, the two sets of spaced apart bands, i.e., a first set formed by bands 1, 3, and 5 and a second set formed by bands 2 and 4, are each directed to a laminating apparatus and two fastener products are simultaneously produced, as discussed above with reference to FIG. 3D.

The stretchable fastener of FIG. 1 may also be formed by the process and apparatus illustrated in FIG. 5.

Figure 6A:
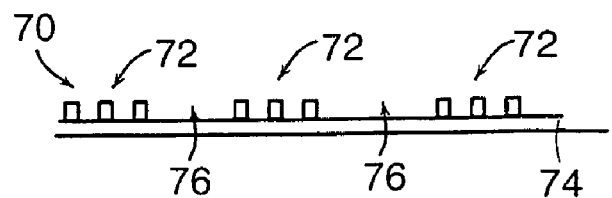
FIG. 6A is a side view of the fastener tape 70 in FIG. 5.
Figure 6B:
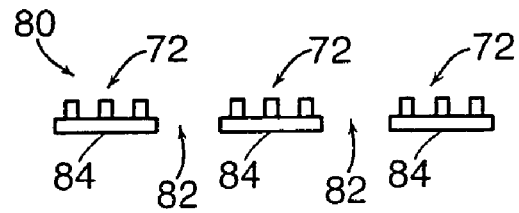
FIG. 6B is a side view of the slit fastener bands 80 in FIG. 5.
Figure 6C:
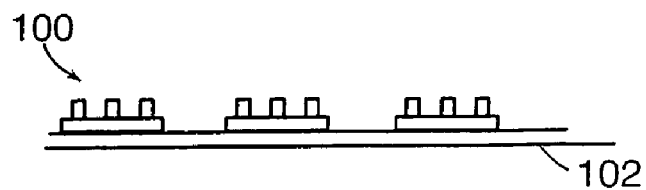
FIG. 6C is a side view of the stretchable fastener 100 in FIG. 5.

Extruder barrel 42 melts and forces molten plastic 40 through a slot-form die 41. The extruded plastic enters nip 44 formed between base roll 48 and mold roll 46. Mold roll 46 contains cavities 45 shaped to form hook-type fastener elements. The hook cavities 45 (FIG. 5A) are arranged in separated bands 50 on the surface of the mold roll 46 (FIG. 5B). Smooth bands 51 that contain no cavities separate the hook cavity bands 50. The width of the cavity bands 50 equals the width of the fastener tape bands w1 and the width of the smooth bands 51 equals the desired spacing between the fastener tape bands w2. The sheet-form fastener material 70 (FIG. 6A) formed in nip 44 has rows of hook fastener elements integrally molded with a base layer alternating with rows of only the base layer. The fastener material 70 travels about a segment of the periphery of mold roll 46 to slitting roll 210. Slitting roll 210 slits and removes the bands of only the base layer 76 thus forming spaced apart bands of fastener tape 80 (FIG. 6B) having fastener elements residing in the hook molds of the mold roll 46. A second extruder 52 introduces molten plastic 49, suitable for molding an elastic web, through a slot-form die 53 into a nip 54 formed diametrically opposite nip 44 between the mold roll 46 and a third roll 55. Molten plastic 49 is squeezed down to a thin film 102 and is applied to the back surface 84 of the fastener bands 80 on the mold roll 46 and fills the empty spaces 82 between the fastener bands. The back surfaces of the spaced apart fastener bands 82 fuse together with the continuous thin film 102 by the heat and pressure generated between the mold roll 46 and third roll 55. The formed composite elastic web with the attached fastener bands 100 (FIG. 6C) is subsequently removed from the third roll 55.

For more detail about the general operation of the in situ molding apparatus of FIG. 5, the reader is referred to U.S. Pat. No. 5,260,015 to Kennedy, et al., which discloses laminates made with loop materials.

The stretchable fastener of FIG. 1 may also be formed by the embodiment illustrated in FIG. 7. Extruder barrel 42 melts and forces molten plastic 40 through a slot-form die 41. The extruded plastic enters the nip 44 between base roll 48 and mold roll 46. The entire outside surface of the mold roll 46 contains cavities 45 shaped to form hook-type fastener elements. The sheet-form fastener material 70 (FIG. 7B) formed in nip 44 has rows of hook fastener elements 106 integrally molded with a base layer 74. The fastener material 70 travels about the periphery of mold roll 46 and is guided by two guide rolls 56 and 58 to slitting rolls 210. Slitting rolls 210 slit the fastener 70 into bands 80 which are then separated by passing through separator 221. The spaced apart fastener bands 80 are then introduced into spaced apart channels 232 formed on the surface of the channeled roll 230 (FIG. 7C). The hook-shaped fastener elements 106 reside in the channels 232 with the hooks engaging the bottom of the respective channel. The channels 232 have a width equal to the fastener band width w1 and are spaced apart by a distance equal to the fastener band spacing w2. The fastener bands are introduced into a nip 242, formed between the channeled roll 230 and a heated pressure roll 250. Simultaneously with the fastener bands, a sheet-form elastic web 240 is introduced into the nip 242. The heated roll 250 presses and fuses the elastic web 240 onto the back surface 84 of the fastener bands 80. The hooks engaging the bottom of the channels 232 are collectively self supporting under the pressure of laminating and assist in producing the laminating pressure by which the bands are joined to the second material. The composite elastic web with the attached fastener bands 100 is then removed from the heated roll 250.

Figure 8:
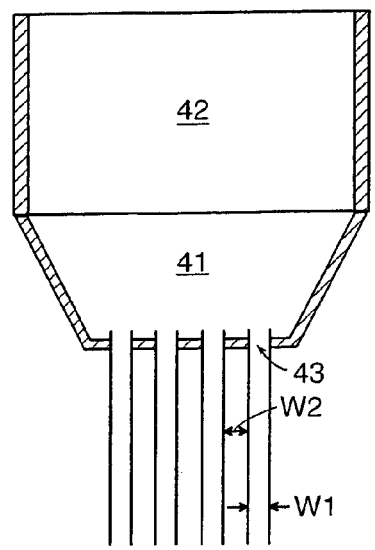
FIG. 8 is a cross sectional view of a slotted die having multiple slot openings.

In the embodiment of FIG. 9, separated fastener bands 80 are formed directly on the mold roll 46 by using a slot form die 41 that has multiple spaced apart slots 43 (FIG. 8). Mold roll 46 contains cavities 45 shaped to form hook-type fastener elements, and the hook cavities 45 (FIG. 5A) are arranged in separated bands 50 on the surface of the mold roll 46 (FIG. 5B). Slots 43 are aligned to inject molten resin into the cavity bands 50 of the mold roll 46, have a width equal to the fastener band width w1, and are spaced apart by a distance equal to the spacing between the fastener tape bands w2. A second slotted die 53 with multiple slots is used in the second extruder 52 to form bands of elastic film 88 filling the spaces 82 between the fastener tape bands 80 (FIG. 9B). The edge margins 89 of the bands of elastic film 88 overlap the edge margins 87 of the fastener bands 80. In some embodiments (FIG. 9C), the edge margins 89 of the bands of elastic film 88 abut the edge margins 87 of the fastener bands 80.

Figure 10:
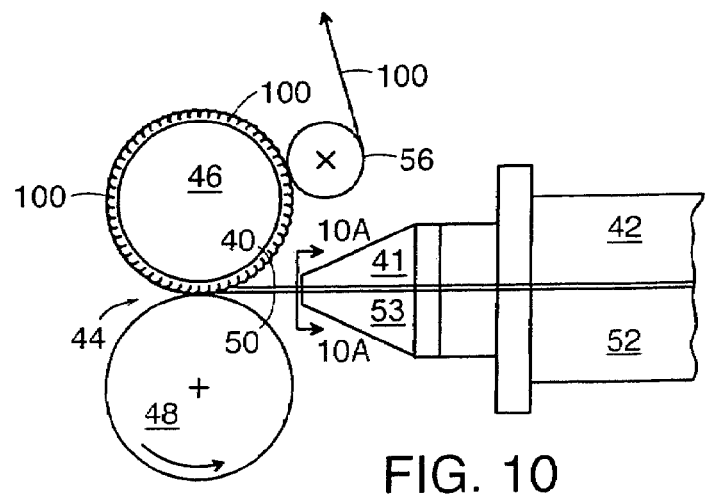
FIG. 10 illustrates another method and an apparatus for forming the stretchable fastener of FIGS. 9B and 9C.
Figure 10A:
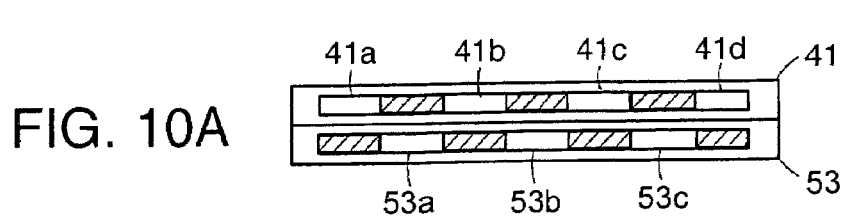
FIG. 10A is a cross sectional view of the two separated slotted dies 41 and 51 of FIG. 10 taken along plane 10A-10A.

In the embodiment of FIG. 10, the bands of elastic film 88 are coextruded with the bands of the fastener tape 80 by using an extruder with separate chambers 42 and 52 and two separate slotted dies 41 and 53 connected to the separate chambers 42 and 52, respectively (FIG. 10B). The two slotted dies 41 and 53 have multiple slot openings 41a to 41d and 53a to 53c, respectively (FIG. 10A). Two different types of molten resin are simultaneously extruded into the same nip 44. The coextruded bands of fastener tape 80 and elastic film 88 are fused at the margins 89 and 87 by the pressure and heat provided by roll 48.

Other features and advantages of this invention may include one or more of the following. A continuous heated belt may be used to apply pressure and heat to the elastic web to cause fusion to the back surface of the fastener bands. Elastic webs having an elongation of at least 300% and recovery of at least 75% may be used. The width of the fastener bands may be between ⅛ to ¼ inch (3.18 to 6.35 mm). The width of the elastic bands may be between ⅛ to ¼ inch (3.18 to 6.35 mm). Narrow fastener bands separated by narrow elastic bands are used to form stretchable fasteners covering a large area. Large area stretchable fasteners may be used to form stretchable bands that provide motion flexibility. A wide stretchable fastener band 18 next to a wide elastic band 19 may be used to form a fastener tab 12 used as part of infant and adult diapers 10 (FIGS. 11 and 11A).

Although each of the above-described examples has referred to hook-shaped fastener elements, any shape suitable for engaging a loop or mesh material, or capable of engaging other fastener elements of like or unlike shape is suitable. For example, U.S. Pat. No. 6,248,276, the full contents of which are hereby incorporated by reference, discloses various suitable fastener elements and methods and apparatus for their manufacture. Briefly, referring to FIG. 12, one example of an alternative fastener shape is fastener element 10 which includes a base 12 and a fastener element 14 extending from the base. (Fastener 10 generally includes an array of fastener elements; a single fastener element is shown for clarity.) Fastener element 14 includes a stem 16 and, at the terminal end of stem 16, a head 18. Head 18 is shaped for engagement with another fastener component, for example a female fastener component having a plurality of loops, a mesh such as an insect screen, or another fastener component similar to fastener 10.

As shown in FIG. 12, head 18 is substantially disc-shaped, including a substantially planar top surface 20, and a substantially planar bottom surface 22 that faces and overhangs base 12. It is desirable that the disc be relatively thin, allowing a cooperating fastener element, e.g., a loop or the wire mesh of a window screen, to penetrate into the disc by flexing the disc material. Preferably, the thickness of the disc is from about 5 to 15% of the equivalent diameter of the disc. If the disc is thinner, it will tend to have reduced cycle life (i.e., durability during repeated engagement and disengagement of the fastener), whereas if the disc is thicker the fastener may exhibit reduced peel strength.

A machine 300 for forming the fastener elements 10 described above is shown in FIG. 13. For a more detailed description the reader is again referred to previously incorporated U.S. Pat. No. 6,248,276. Briefly, a supply roll 302 introduces a continuous supply of a stem-carrying base 12 (FIG. 12) into the machine 300. Stem-carrying base 12 is formed of a thermoformable polymer. In a previous manufacturing step, roll 302 was wound up as the take-up roll at a molding station (not shown, but one example of a stem molding method is similar to the hook molding operation described above with reference to FIGS. 5 and 7 wherein the mold cavities have a straight stem shape instead of a hook shape) at which stems were integrally molded onto base 12.

Alternatively, as discussed further below, the stem-carrying base 12 has already been slit, separated and joined to an elastic web using, e.g., one of the methods and apparatus previously described with reference to FIGS. 3, 3D, 5, 7 or 9.

The supply roll 302 is unwound by drive mechanism 306, which conveys stem-carrying base 12 into optional pre-heating area 308 which raises the temperature of the stem-carrying base 12 to a pre-heat temperature that is above room temperature but much lower than the temperature at which the polymer melts or deforms. This pre-heating allows the tips of the stems to be heated to a predetermined softening temperature more quickly during the next step of the process.

Next, the base 12 moves to heating device 310, which heats only a distal portion, i.e., a portion furthest from base 12, of the stems. The remainder of the stem remains relatively cool and thus relatively rigid. The distal portion is heated to a softening temperature at which it can be formed into a desired head shape. To ensure that only the distal portion of each stem is heated to the softening temperature, it is preferred that heating device 310 include a non-contact heat source that is capable of quickly elevating the temperature of material that is very close to the heat source, without raising the temperature of material that is relatively further away from the heat source. Suitable non-contact heat sources include flame heaters, electrically heated nichrome wire, and radiant heater blocks. To heat the distal portion to the softening temperature without contact, the heat source typically must be at a relatively high temperature. For example, if the softening temperature is from about 100 to 140° C., the temperature of the heat source will generally be from about 300 to 1000° C. and the heat source will be positioned from about 0.1 to 30 mm from the tips of the stems.

After the distal portions of the stems have been heated, the base 12 moves to conformation head 312, at which base 12 passes between conformation roll 314 and drive roll 316. Conformation roll 314 forms the distal portion of the stems into a desired head shape, as will be described in further detail below, while drive roll 316 advances base 12 and flattens it against roll 314 to enhance head uniformity. It is preferred that the temperature of conformation roll 314 (the forming temperature) be lower than the softening temperature. Maintaining the conformation roll 314 at this relatively low temperature has been found to allow the conformation roll to flatten the spherical ("ball-shaped") heads that are generally formed during the previous heating step into a desired head shape. Spherical heads are generally undesirable, as such heads tend not to provide secure engagement with a mating fastener. A low forming temperature also prevents adhesion of the thermoformable polymer to the conformation roll. Generally, to obtain the desired forming temperature it is necessary to chill the conformation roll, e.g., by running cold water through a channel in the center of the roll, to counteract heating of the conformation roll by the heat from the distal portions of the stems. If further cooling is needed to obtain the desired forming temperature, the drive roll may be chilled in a similar manner.

The surface texture of conformation roll 314 will determine the shape of the heads that are formed. If disc-shaped heads having a smooth surface (as illustrated in FIG. 12) are desired, the surface texture will be smooth and flat. If a sandpaper-like surface is desired, the surface texture of the conformation roll will be sandpaper-like. If mushroom-shaped (domed) heads are desired, the conformation roll will include a plurality of substantially hemispherical indentations ("dimples") to form the dome portion of the heads. Other shapes are of course possible by using a conformation roll with a surface shape corresponding to the desired fastener head shape.

The spacing of the conformation roll 314 from the drive roll 316 is selected to deform distal portions of the stems to form the desired head shape, without excessive damage to the unheated portion of the stems. It is also preferred that the spacing be sufficiently small so that the drive roll flattens base 12 and provides substantially uniform contact pressure of the stem tips against the conformation roll. Preferably, the spacing is approximately equal to the total height of the stem less the length of the heated distal portion.

Next, the base 12 moves to a cooling station 318. Cooling station 318 cools the formed heads, e.g., by cool air, preventing further deformation of the heads. Preferably, the heads are cooled to approximately room temperature. The cooled base is then moved through driving station 320 and is then passed through a slitter 322, a separator 324, and a joining station 326 where separated bands of the product are joined to an elastic web. Slitter 322, separator 324, and joining station 326, can be apparatus similar to those described above, e.g., with reference to FIGS. 3 or 3D, and operate in a similar manner.

In an alternative arrangement, a base having stems only, is formed, slit and joined to a stretchable web as described above with reference to FIGS. 3, 3D, 5, 7, and 9, and the stems are later formed into a fastener shape as described above with reference to FIGS. 12 and 13. The resulting fastener product 100' is similar to that shown, e.g., in FIGS. 1-1D but having fastener elements similar to that illustrated in FIG. 12.

A number of embodiments of the invention have been described. Nevertheless, it will be understood that various modifications may be made without departing from the spirit and scope of the invention. Accordingly, other embodiments are within the scope of the following claims.

What is claimed is:

1. A method of forming a stretchable fastener product comprising:
   providing a sheet-term fastener tape comprising a base of synthetic resin, and an array of loop-engagable fastener elements integrally molded with and extending from a first surface of the base;
   processing said fastener tape including slitting to form longitudinally extending bands of fastener tape and to space said fastener bands transversely apart; and
   attaching said transversely spaced apart fastener bands to a sheet form elastic web to form the stretchable fastener product, wherein the attaching of the transversely spaced apart fastener bands to the elastic web comprises supporting the spaced apart fastener bands on a support roll wherein the loop-engageable fastener elements are in contact with a surface of the support roll, while simultaneously pressing and heating the elastic web against a second surface of the base of the fastener bands, the support roll having circumferential recesses configured to support the fastener bands and to position the second surface of the base of the fastener bands at the surface of the support roll.

2. The method of claim 1 in which the elastic web extends widthwise across the transversely spaced apart fastener bands as well as across spaces between adjacent spaced apart bands.

3. The method of claim 1 in which said step of attaching includes providing a number of separate elastic webs, including at least one elastic web attached to extend across each space between adjacent transversely spaced apart fastener bands.

4. The method of claim 1 wherein transversely spaced apart bands are formed by passing the slit fastener tape bands through a separator that separates the bands and spaces them transversely apart.

5. The method of claim 1 wherein the transversely spaced apart fastener bands are attached to the elastic web by thermal fusion.

6. The method of claim 1 wherein the transversely spaced apart fastener bands are attached to the elastic web by ultrasonic welding.

7. The method of claim 1 wherein the fastener elements comprise relatively stiff stems and hook-shaped heads.

8. The method of claim 1 wherein a heated laminating roll is arranged to press the elastic web against the second surface of the base of the fastener bands to promote lamination.

9. The method of claim 1 in which the fastener elements are molded of resin selected from the group consisting of polyester, polyethylene, polypropylene, polyamide and copolymers and alloys thereof.

10. The method of claim 1 in which the second material is comprised of a resilient resin having an elongation in the range of 50% to 300% and a recovery of at least 75%.

11. The method of claim 1 in which the second material is selected from the group consisting of thermoplastic elastomers, thermoplastic polyurethanes, elastomeric copolymers containing polyethylene terephthalate PET, thermoplastic olefins, and natural or synthetic rubber.

12. The method of claim 1 in which each of the fastener bands and spaces between the fastener bands has a width less than or equal to ¼ inch.

13. The method of claim 1 in which each of the fastener bands and spaces between the fastener bands has a width greater than ¼ inch.

14. The method of claim 1 in which each of the fastener bands has a width less than or equal to ¼ inch, and each of the spaces between the fastener bands has a width greater than or equal to ¼ inch.

15. The method of claim 1 in which each of the fastener bands has a width greater than or equal to ¼ inch, and each of the spaces between the fastener bands has a width less than or equal to ¼ inch.

16. The method of claim 1 wherein said array of loop-engageable fastener elements has a density of the order of 500 or more fastener elements per square inch.

17. The method of claim 16 wherein said array of loop-engageable fastener elements has a density of the order of 1000 or more fastener elements per square inch.

18. The method of claim 1 in which a backing is attached to the second surface of the base of the fastener bands.

19. The method of claim 18 in which the backing of the fastener bands comprises a heat-sensitive adhesive, the method including the step of activating the adhesive before engagement with the elastic web.

20. A method of forming a stretchable fastener product comprising:
   introducing moldable first material to a continuously rotating mold roll to form a sheet-form fastener having a base conforming to a surface of the mold roll and multiple rows of molded fastener elements integral with a first surface of the base, the rows extending in a longitudinal direction of the sheet-form fastener, the fastener elements formed by mold cavities of the mold roll;
   slitting the thus-formed sheet-form fastener into longitudinally extending fastener bands carrying multiple rows of the fastener elements; removing the fastener bands froms the mold roll, and passing the fastener bands through a separating device that develops space between the adjacent fastener bands transversely to the longitudinal direction; and subsequently
   introducing the fastener bands onto a surface of a support roll having circumferential recesses configured to support the fastener bands and to position a second surface of the base of the fastener bands at the surface of the support roll, and joining a web of a second material to the fastener bands by pressure and heat while the fastener bands are On the support roll, the second material being resiliently extensible to form the stretchable fastener product.

21. The method of claim 20 in which the second material is resiliently extensible in the transverse direction.

22. The method of claim 20 in which the fastener elements are loop-engageable hooks molded of synthetic resin of density of the order of 500 or more fastener elements per square inch, the elements having relatively stiff stems of greater cross-section than their loop-engageable hooks, the hooks of the fastener elements of a given band engaging the bottom of the respective recess and being collectively self supporting under the pressure of laminating, serving to assist in producing laminating pressure by which the fastener bands are joined to the second material.

23. The method of claim 22 in which the fastener elements are of density of the order of 1000 or more fastener elements per square inch.

24. The method of claim 20 in which a heated laminating roll is arranged to press the second material against the second surface of the base of the fastener bands to promote lamination.

25. The method of claim 20 in which a heat-sensitive adhesive backing is attached to the second surface of the base of the fastener bands, the method including the step of activating the adhesive before engagement with the second material.

26. The method of claims 20 in which the second material is comprised of a resilient resin having an elongation in the range of 50% to 300% and a recovery of at least 75%.

27. The method of claims 20 in which the second material is selected from the group consisting of thermoplastic elastomers, thermoplastic polyurethanes, elastomeric copolymers containing polyethylene terephthalate PET, thermoplastic olefins, and natural or synthetic rubber.

28. The method of claims 20 in which each of the fastener bands and spaces between the fastener bands has a width less than or equal to ¼ inch.

29. The method of claims 20 in which each of the fastener bands and spaces between the fastener bands has a width greater than ¼ inch.

30. The method of claims 20 in which each of the fastener bands has a width less than or equal to ¼ inch, and each of the spaces between the fastener bands has a width greater than or equal to ¼ inch.

31. The method of claims 20 in which each of the fastener bands has a width greater than or equal to ¼ inch, and each of the spaces between the fastener bands has a width less than or equal to ¼ inch.

* * * * *

UNITED STATES PATENT AND TRADEMARK OFFICE
CERTIFICATE OF CORRECTION

| | | |
|---|---|---|
| PATENT NO. | : 7,223,314 B2 | |
| APPLICATION NO. | : 10/242900 | |
| DATED | : May 29, 2007 | |
| INVENTOR(S) | : George A. Provost | |

It is certified that error appears in the above-identified patent and that said Letters Patent is hereby corrected as shown below:

(73) Assignee: "Velero Industries B.V., Caracao" should be --Velcro Industries B.V., Curacao--

Col. 14, line 14 "On the" should be --on the--

Signed and Sealed this

Fifth Day of August, 2008

JON W. DUDAS
*Director of the United States Patent and Trademark Office*

UNITED STATES PATENT AND TRADEMARK OFFICE
CERTIFICATE OF CORRECTION

PATENT NO. : 7,223,314 B2
APPLICATION NO. : 10/242900
DATED : May 29, 2007
INVENTOR(S) : George A. Provost It is certified that error appears in the above-identified patent and that said Letters Patent is hereby corrected as shown below:

Claim 1, column 12, line 42:
  delete "sheet-term" and replace with --sheet-form--.

Claim 1, column 12, line 43:
  delete "loop-engagable" and replace with --loop-engageable--.

Claim 10, column 13, line 24:
  delete "second material" and replace with --elastic web--.

Claim 11, column 13, line 27:
  delete "second material" and replace with --elastic web--.

Claim 20, column 13, line 60:
  delete "introducing moldable" and replace with --introducing a moldable--.

Claim 20, column 14, line 4:
  delete "froms" and replace with --from--.

Claim 20, column 14, line 15:
  delete "On" and replace with --on--.

Claim 26, column 14, line 43:
  delete "claims" and replace with --claim--.

Claim 27, column 14, line 46:
  delete "claims" and replace with --claim--.

Claim 28, column 14, line 51:
  delete "claims" and replace with --claim--.

Claim 29, column 14, line 54:
  delete "claims" and replace with --claim--.

UNITED STATES PATENT AND TRADEMARK OFFICE
CERTIFICATE OF CORRECTION

PATENT NO.       : 7,223,314 B2
APPLICATION NO.  : 10/242900
DATED            : May 29, 2007
INVENTOR(S)      : George A. Provost It is certified that error appears in the above-identified patent and that said Letters Patent is hereby corrected as shown below:

Claim 30, column 14, line 57:
    delete "claims" and replace with --claim--.

Claim 31, column 14, line 62:
    delete "claims" and replace with --claim--.

Signed and Sealed this

Seventeenth Day of February, 2009

JOHN DOLL
*Acting Director of the United States Patent and Trademark Office*